United States Patent [19]

Ochsner

[11] Patent Number: 4,544,714

[45] Date of Patent: Oct. 1, 1985

[54] ODORANT OXIMES

[75] Inventor: Paul A. Ochsner, Geneva, Switzerland

[73] Assignee: Givaudan Corporation, Clifton, N.J.

[21] Appl. No.: 461,053

[22] Filed: Jan. 26, 1983

[30] Foreign Application Priority Data

Feb. 3, 1982 [CH] Switzerland .......................... 645/82

[51] Int. Cl.[4] ...................... C11B 9/00; C07C 131/00

[52] U.S. Cl. ............................... 252/522 R; 564/268; 252/174.11; 131/276; 424/69; 424/70; 424/76

[58] Field of Search .................... 252/522 R; 564/268

[56] References Cited

U.S. PATENT DOCUMENTS

| | | | |
|---|---|---|---|
| 3,453,317 | 7/1969 | Marbet et al. | 260/476 |
| 3,637,533 | 1/1972 | Dahill | 252/522 R |
| 4,052,194 | 10/1977 | Wilcox | 564/268 X |
| 4,426,321 | 1/1984 | Ochsner | 568/840 X |

FOREIGN PATENT DOCUMENTS

| | | | |
|---|---|---|---|
| 0045861 | 2/1982 | European Pat. Off. | 564/268 |
| 1305994 | 9/1962 | France . | |
| 1461149 | 1/1972 | United Kingdom . | |

*Primary Examiner*—Thomas A. Waltz

*Attorney, Agent, or Firm*—Robert F. Tavares

[57] ABSTRACT

This invention discloses a number of novel odorant oximes having from 11 to 14 carbon atoms, processes for making same, and odorant compositions containing same.

16 Claims, No Drawings

ODORANT OXIMES

THE INVENTION

This invention is concerned with novel compounds of the formula:

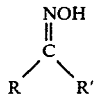

I wherein:

R is a $\Delta^{3,4}$ alkenyl group of six to twelve carbons, and

R′ is an alkyl group of one to four carbons provided that the total number of carbon atoms in the compound is between eleven and fourteen.

The invention is also concerned with processes for the manufacture of these compounds and their use as odorants.

Formula I is intended to embrace the syn- and anti-forms of the oximes. The groups denoted by R and R′ can be straight-chain or branched-chain.

DESCRIPTION OF THE PREFERRED EMBODIMENTS

As defined, formula I is intended to embrace both oxime isomers with the anti form being preferred. The lower molecular weight oximes wherein the sum of R and R′ contain ten to twelve carbon atoms are preferred with the ten to eleven carbon atom analogs being especially preferred.

The novel oximes of formula I can be prepared by a process which comprises reacting a ketone of the formula

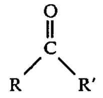

II wherein R and R′ are as defined above, with hydroxylamine or a salt thereof.

The reaction of a ketone of formula II with hydroxylamine or a salt thereof can be carried out according to methods known per se; see, for example, Organikum, Organisch-chemisches Grundpraktikum, Collective Authors; 7th Edition; VEB Deutscher Verlag der Wissenschaften; Berlin 1967, 375. The hydroxylamine or a salt thereof (e.g. the hydrochloride or sulphate) is reacted in pyridine-containing alkaline solution or in aqueous alkaline solution with the ketone of formula II. The reaction is preferably carried out at the reflux temperature of the reaction mixture. The resulting oximes can be purified by distillation.

The ketone starting materials of formula II are known or can be prepared according to known methods, for example, by chain-lengthening of simple, commercial ketones (e.g. by means of allyl halides).

The compounds of formula I have particular organoleptic properties which make them especially suitable as odorant substances.

The oximes provided by the present invention are distinguished by a particular combination of perfumistically valuable properties. They are all either colourless (or at most slightly coloured), readily accessible, the individual batches are constant in odour, non-irritating, stable, and easy to handle.

The compounds of formula I are generally reminiscent with respect to odour of notes of blackcurrants, sage, ivy, and grapefruit; on the basis of their natural odour notes and their fixation (long-lasting effect, especially with respect to freshness) they are suitable, in particular, for modifying known compositions, examples of such compositions being:

(a) flowery compositions in which, for example, the citrus notes are to be intensified (e.g., for cologne types and the like, as well as essences), (b) fruity compositions, for example of the currant type (essence types), compositions of the feminine as well as of the masculine direction, (c) compositions with green notes, where especially a desired natural effect is produced, and finally (d) compositions in which generally the character of natural oils is striven for (e.g. lilac or lavender).

Especially interesting compounds of formula I are:

5-Ethyl-7-nonen-4-one oxime

Odour: after blackcurrants, natural, earthy, herby.

2,4,4,7-Tetramethyl-6-octen-3-one oxime

Odour: after blackcurrants, sage, lavender, grapefruit, leek-like.

4,7-Dimethyl-6-nonen-3-one oxime

Odour: after fresh vegetables, after peas, daisies, privet shrub, good fixation.

3-Ethyl-6-methyl-5-octen-2-one oxime:

Odour: after fresh vegetables, after ivy, privet shrub.

Examples of other compounds of formula I are:

2,4,4,6-Tetramethyl-6-hepten-3-one oxime

Odour: after fresh vegetables, after tomato leaves, after blackcurrants, very natural.

3,3,6-Trimethyl-5-octen-2-one oxime

Odour: after grapefruit, currants, good fixation.

2,2,7-Trimethyl-6-nonen-3-one oxime

Odour: after marsh marigolds, very natural.

The compounds of formula I combine with numerous known natural or synthetic ingredients of odorant substance compositions, whereby the range of the natural ingredients can embrace not only readily-volatile but also semi-volatile and slightly-volatile components and the range of the synthetic ingredients can embrace representatives from almost all classes of substances, as will be evident from the following compilation:

*Natural products* such as angelica seed oil, tree moss absolute, basil oil, mugwort oil, bergamot oil, castoreum, acetylated cedarwood oil (e.g. Vertofix ® IFF or Cedartone TM Givaudan), coriander oil, oak moss, elemi oil, galbanum oil, geranium oil, jasmine absolute and its substitute, camomile oil, lavandin oil, lavender oil, mandarin oil, mastix absolute, clove bud oil, neroli oil, patchouli oil, petitgrain oil Paraguay, rose oil, rosemary oil, sandalwood oil, styrax, vetiver oil, wormwood oil, ylang-ylang oil, hyssop oil, civet oil and lemon oil.

Alcohols such as citronellol, dimethylbenzylcarbinol, Dimetol ® Givaudan (2,6-dimethyl-2-heptanol), geraniol, linalool, menthol, 3-methyl-5-(2′,2′,3′-trimethylcyclopent-3′-en-1′-yl)-pentan-2-ol (Sandalore ® Givaudan), nerol, phenylethyl alcohol, phenylpropyl alcohol, natural rhodinol, terpineol, α-terpineol, 2,2,8-trimethyl-7-nonen-3-ol and cinnamic alcohol.

Aldehydes such as α-amylcinnamaldehyde, citral, cyclamen aldehyde, decanal, 3,5-dimethyl-cyclohex-3-ene-carboxaldehyde, n-dodecanal, heliotropin, α-hexylcinnamaldehyde, hydroxycitronellal, methylnonylacetaldehyde, p-tert.butyl-α-methyl-dihydro-cinnamic aldehyde (e.g. Lilial ® Givaudan and n-undecen-10-al.

Ketones such as acetylcedrene, allyl ionone, p-hydroxybenzyl-acetone, α-ionone, 2,4,4,7-tetramethyl-6,8-nonadien-3-one, p-methylacetophenone, methyl ionone and 1,2,3,4-tetrahydro-1,1-dimethyl-4-propionyl-naphthalene.

Esters such as ethyl acetoacetate, 3-ethyl-1,1-dimethyl-cyclohex-3-ene-2-carboxylic acid ethyl ester (Givescone ® Givaudan), 3-ethyl-1,1,4-trimethyl-cyclohex-3-ene-2-carboxylic acid ethyl ester (Myrascone TM Givaudan), allyl phenoxyacetate, amyl salicylate, benzyl acetate, benzyl salicylate, bornyl acetate, cedryl acetate, cinnamyl formate, cis-3-hexenyl acetate, cis-3-hexenyl benzoate, geranyl acetate, hexyl salicylate, isobutyl salicylate, linalyl acetate, linalyl anthranilate, methyl dihydrojasmonate, 4-[4-methyl-3-pentenyl]-cyclohex-3-en-1-yl-carbinyl acetate (e.g. Myraldylacetat TM Givaudan), oxyoctalene formate Giv. ($\Delta^1$-1,5,9,10-tetramethyl-5-formoxy-octalene), phenylethyl acetate, styrallyl acetate, terpenyl acetate and p-tert.butylcyclohexyl acetate.

Lactones such as coumarin, γ-decalactone, γ-dodecalactone, γ-nonalactone and γ-undecalactone.

Various additonal components often used in perfumery such as acetaldehyde propylphenyl ethyl acetal, cyclocitrylideneacetonitrile, 1,1-dimethyl-4-acetyl-6-tert.butylindane, dodecahydro-3a,6-6-9a-tetramethyl(2,1-b)furan, eugenol, Galaxolid IFF (7-acetyl-1,1,3,4,4,6-hexamethyl-tetralin), indole, isobutylquinoline, p-menthane-8-thiol-3-one, methyleugenol, methyl 1-methyl-cyclododecyl ether (e.g. Madrox TM Givaudan) and musk compounds [musk ketone, 12-oxahexadecanolide (e.g. Musk 174 TM Naarden) and 8,12-oxido-13,14,15,16-tetranorlabdane (Fixateur 404 TM )].

The compounds of formula I can be used in compositions within wide limits which, for example, can extend from 0.1% in the case of detergents to 50% in the case of alcoholic solutions. It will be appreciated that these values are not limiting values, since the experienced perfumer can also achieve effects with even lower concentrations or can synthesize novel complexes with still higher concentrations. The preferred concentrations range between 0.5% and 25%. The compositions produced with the compounds of formula I can be used for all kinds of perfumed consumer goods (eau de cologne, eau de toilette, essences, lotions, creams, shampoos, soaps, salves, powders, deodorants, detergents, tobacco etc).

The compounds of formula I can accordingly be used for the production of compositions and, as will be evident from the foregoing compilation, a wide range of known odorant substances can be used. In the production of such compositions, the known odorant substances referred to earlier can be used according to methods which are known to the perfumer such as, for example, according to W. A. Poucher, Perfumes, Cosmetics and Soaps 2, 7th Edition, Chapman and Hall, London 1974.

ILLUSTRATION OF THE PREFERRED EMBODIMENTS

The following Examples illustrate the present invention:

EXAMPLE 1

14.8 g of hydroxylamine sulphate are dissolved in 30 ml of water in a round flask provided with a stirrer, thermometer and condenser. While 29 g of 33% sodium hydroxide are added thereto, the temperature is held at 25° C. by cooling. There is then slowly added dropwise thereto at room temperature a solution of 27 g of 5-ethyl-7-nonen-4-one (boiling point: 74° C./5 mmHg; $n_D^{20}$=1.4407) in 50 ml of ethanol. The mixture is thereupon held at reflux temperature for 1 hour. After cooling, the mixture is poured into ice/water, taken up in ether and washed neutral. The solvent is distilled off and there are obtained 26.8 g of crude oxime which are fractionally distilled.

Boiling point of the pure 5-ethyl-7-nonen-4-one oxime (10.5 g): 118° C./5 mmHg; $n_D^{20}$=1.4691.

In an analogous manner, from 41.7 g of 4,7-dimethyl-6-nonen-3-one (boiling point 75° C./6 mmHg; $n_D^{20}$=1.4472) and 20.5 g of hydroxylamine sulphate there are obtained 29.1 g of 4,7-dimethyl-6-nonen-3-one oxime; boiling point 85° C./0.5 mmHg; $n_D^{20}$=1.4762;

from 25.5 g of 3,3,6-trimethyl-5-octen-2-one (boiling point 75° C./6 mmHg; $n_D^{20}$=1.4500) and 13.2 g of hydroxylamine sulphate there are obtained 8 g of 3,3,6-trimethyl-5-octen-2-one oxime; boiling point 70° C./0.15 mmHg; $n_D^{20}$=1.4790; and from 32.6 g of 2,2,7-trimethyl-6-nonen-3-one (boiling point 88° C./5 mmHg; 1.4448) and 14.8 g of hydroxylamine sulphate there are obtained 1.1 g of 2,2,7-trimethyl-6-nonen-3-one oxime; boiling point 86°-87° C./0.45 mmHg; $n_D^{20}$=1.4715.

EXAMPLE 2

A solution of 20 g of hydroxylamine hydrochloride and 20 g of pyridine in 200 ml of ethanol is held at reflux temperature for 1 hour in a round flask provided with a stirrer, thermometer and condenser. 20 g of 2,4,4,7-tetramethyl-6-octen-3-one (boiling point 76° C./5 mmHg; $n_D^{20}$=1.4469) are thereupon added thereto and the mixture is held at reflux temperature for a further 3 hours. The majority of the ethanol is thereupon distilled off. After cooling, the residue is poured into ice/water and taken up in ether. The ether solution is washed firstly with water, then with 5% hydrochloric acid in order to eliminate the excess pyridine and then again with water until it is neutral. After evaporation of the ether, there are obtained 18 g of crude product. 15.3 g of ketone starting material are recovered by distillation. The residue (1.2 g) consists of 2,4,4,7-tetramethyl-6-octen-3-one oxime, $n_D^{20}$=1.4770.

In an analogous manner, from 30 g of 3-ethyl-6-methyl-5-octen-2-one (boiling point 77° C./6 mmHg; $n_D^{20}$=1.4476), 30 g of hydroxylamine hydrochloride and 30 g of pyridine there are obtained 12.8 g of 3-ethyl-6-methyl-5-octen-2-one oxime; boiling point 77° C./0.2 mmHg; $n_D^{20}$=1.4750; and from 34 g of 2,4,4,6-tetramethyl-6-hepten-3-one (boiling point 62° C./5 mmHg; $n_D^{20}$=1.4445), 34 g of hydroxylamine hydrochloride and 34 g of pyridine there are obtained 1.1 g of 2,4,4,6-tetramethyl-6-hepten-3-one oxime; boiling point 75° C./0.3 mmHg; $n_D^{20}$=1.4745.

EXAMPLE 3

Perfumery base having a general flowery direction:

| | Parts by weight |
|---|---|
| Terpineol | 260 |
| Hydroxycitronellal | 200 |
| Phenylethyl alcohol | 200 |
| Cinnamic alcohol substitute | 100 |
| Phenylpropyl alcohol | 100 |
| Cinnamyl formate | 20 |
| Linalool | 15 |
| Terpenyl acetate | 10 |
| Musk ketone (1-acetyl-2,6-dimethyl-4-tert.butyl-3,5-dinitrobenzene) | 10 |
| Geranyl acetate | 10 |
| Jasmine synthetic | 10 |
| Eugenol | 5 |
| Undecalactone | 5 |
| p-Methylacetophenone | 5 |
| Indole [10% in dipropylene glycol (DPG] | 5 |
| C—10-aldehyde (n-decanal) (10% in DPG) | 5 |
| | 960 |

An addition of 60 parts of 5-ethyl-7-nonen-4-one oxime confers to this base, which originally exhibits a direction more of lilac, much more fruity, sweet and warmer notes. The novel base is now pleasantly oriental and, in addition, a note in the direction of orchids can be recognized. The novel oxime combines excellently with the ingredients of this base.

EXAMPLE 4

Perfumery base in the direction of tea:

| | Parts by weight |
|---|---|
| Bergamot oil | 150 |
| Linalool | 100 |
| Hydroxycitronellal | 100 |
| Methyl dihydrojasmonate | 60 |
| Patchouli oil | 40 |
| Basil oil | 30 |
| Methyleugenol | 20 |
| β-Ionone | 20 |
| Formiate oxyoctaline TM Giv (3,4,5,6,7,8,9,10-octahydro-1,6,9,10-tetramethyl-5-formoxynaphthalene) | 10 |
| Galaxolide ® IFF (1,3,4,6,7,8-hexahydro-4,6,6,7,8,8-hexamethylcyclopenta-γ-2-benzopyran) | 10 |
| Bornyl acetate | 10 |
| Corps Lavande TM Giv (2,2,8-trimethyl-7-nonen-3-ol) | 10 |
| Tree moss absolute colourless | 10 |
| lemon oil | 10 |
| Vertofix ® IFF (acetylcedrene) | 10 |
| Indole (10% in DPG) | 10 |
| DPG | 350 |
| | 950 |

If 50 parts of 5-ethyl-7-nonen-4-one oxime are added to this chypre base, then it is modified surprisingly in the direction of tea. It is now fresher, greener, more spicy and more herby, thus having the very typical aspect of Chinese smoke-tea.

EXAMPLE 5

Perfumery chypre base:

| | Parts by weight |
|---|---|
| Hydroxycitronellal | 100 |
| Bergamot oil | 80 |
| Methyl dihydrojasmonate | 80 |
| α-Hexylcinnamaldehyde | 80 |
| Phenylethyl alcohol | 80 |
| Tree moss absolute (colourless) | 40 |
| Patchouli oil | 40 |
| Linalool | 40 |
| α-Ionone | 40 |
| Musk ketone (1-acetyl-2,6-dimethyl-4-tert.butyl-3,.5-dinitrobenzene) | 40 |
| Vetiver oil | 20 |
| Sandalwood oil | 20 |
| Benzyl acetate | 20 |
| Styrallyl acetate | 5 |
| Undecalactone | 5 |
| C—11-aldehyde (10% in DPG) (ω-undecenal) | 5 |
| Civet oil (10% in DPG) | 5 |
| DPG | 200 |
| | 900 |

If 100 parts of 5-ethyl-7-nonen-4-one oxime are added to the foregoing chypre base, then the resulting base is much more powdery, more fruity, also more woody and therewith warmer. A slight spicy undertone confers to the resulting chypre base a very individual element which can be used very well in modern perfumery.

EXAMPLE 6

Perfumery green base:

| | Parts by weight |
|---|---|
| Bergamot oil | 200 |
| Labienone ® Giv (2,4,4,7-tetramethyl-6,8-nonadien-3-one) | 200 |
| Tetrascone ® Giv (1,2,3,4-tetrahydro-1,1-dimethyl-4-propionylnaphthalene) | 100 |
| Linalyl acetate | 100 |
| α-Hexylcinnamaldehyde | 100 |
| Benzyl salicylate | 100 |
| Methyl dihydrojasmonate | 60 |
| Basil oil | 30 |
| Linalyl anthranilate | 20 |
| Mastix oil | 10 |
| Corps Cassis ® Giv (8-mercapto-p-menthane-3-one) | 5 |
| Galbanum oil | 5 |
| DPG | 50 |
| | 980 |

An addition of 20 parts of 2,4,4,7-tetramethyl-6-octen-3-one oxime surprisingly introduces into this green base a very pleasant, fruity note which is very strongly reminiscent of grapefruit. Therewith, the base is modified powerfully; whereas the original base is generally flowery-green, the novel base is altered in an original manner in the direction of modern cologne. It is much fresher and substantially more powerful.

EXAMPLE 7

Perfumery base in the direction of linden flower:

| | Parts by weight |
|---|---|
| Hydroxycitronellal | 150 |
| Lilial ® Giv (p-tert.butyl-α-methyl-hydrocinnamaldehyde | 150 |
| Linalool | 150 |
| DPG | 100 |
| α-Ionone | 100 |
| Phenylethyl alcohol | 50 |
| n-Hexyl salicylate | 40 |
| Linalyl anthranilate | 35 |
| Galbanum synthetic | 20 |

-continued

| | Parts by weight |
|---|---|
| Camomile oil Roman | 5 |
| | 800 |

If 200 parts of 4,7-dimethyl-6-nonen-3-one oxime are added to this flowery base, which is primarily generally flowery, it is altered very pleasantly in the direction of linden flower. A very fresh, green and at the same time much softer note now appears. Moreover, the flowery effect is intensified.

EXAMPLE 8

Perfumery base in the direction of cyclamen:

| | Parts by weight |
|---|---|
| DPG | 260 |
| Phenylethyl alcohol | 150 |
| Cyclamen aldehyde | 100 |
| Linalyl acetate | 80 |
| Geraniol | 80 |
| Benzyl acetate | 70 |
| Hydroxycitronellal | 50 |
| a-Ionone | 50 |
| α-Amylcinnamaldehyde | 50 |
| Linalool | 40 |
| C—12-aldehyde (lauric) (10% in propylene glycol) | 20 |
| | 950 |

If 50 parts of 4,7-dimethyl-6-nonen-3-one oxime are added to this base, then the base becomes substantially greener, fresher and more flowery. The typical cyclamen aspect is underlined in a very advantageous manner.

An addition of 50 parts of 3-ethyl-6-methyl-5-octen-2-one oxime brings into prominence a fruity-fresh note which combines very pleasantly with the flowery note.

EXAMPLE 9

Perfumery base in the direction of chypre:

| | Parts by weight |
|---|---|
| DPG | 150 |
| a-Ionone | 100 |
| Phenylethyl alcohol | 100 |
| Corps Lavande ® Giv (2,2,8-trimethyl-7-nonen-3-ol) | 60 |
| α-Hexylcinnamaldehyde | 60 |
| Fixolide ® Giv (7-acetyl-1,1,3,4,4,6-hexamethyltetralin) | 60 |
| Linalyl acetate | 60 |
| 1-Methylcyclododecyl methyl ether | 60 |
| Benzyl acetate | 30 |
| Cedartone (acetylcedrene) | 30 |
| Baccartol ® Giv (citronellal-acetone condensation product) | 30 |
| Tree moss absolute colourless | 20 |
| Styrallyl acetate | 20 |
| Petitgrain synthetic | 20 |
| Galbanum synthetic | 20 |
| Hydroxycitronellal | 15 |
| Ylang synthetic | 10 |
| Dimetol ® Giv (2,6-dimethyl-2-heptanol) | 10 |
| Styrax synthetic | 10 |
| Mugwort oil | 10 |
| Isobutylquinoline (10% in DPG) | 5 |
| C—11-aldehyde (ω-undecanal) (10% in DPG) | 5 |
| Indole (10% in DPG) | 5 |
| Clove bud oil | 5 |
| Undecalactone | 3 |

-continued

| | Parts by weight |
|---|---|
| Isoeugenol | 2 |
| | 900 |

If 100 parts of 3-ethyl-6-methyl-5-octen-2-one oxime are added to this perfumery chypre base, then its odour character is intensified in an advantageous manner. There results a leather-like, spicy side-note which confers much more volume and life to the composition. It is now very well suited for man's lines.

EXAMPLE 10

Perfumery base in the direction of magnolia:

| | Parts by weight |
|---|---|
| Lilial ® (p-tert.butyl-α-methyl-hydrocinnamaldehyde | 200 |
| Hydroxycitronellal | 170 |
| Nerol | 150 |
| Cinnamic alcohol | 100 |
| Ylang-ylang oil | 100 |
| Bergamot oil | 60 |
| Eugenol | 50 |
| Heliotropin | 40 |
| Terpineol | 30 |
| Citral | 20 |
| Jasmine substitute | 10 |
| Benzyl acetate | 10 |
| Neroli oil | 10 |
| Cyclamen aldehyde | 10 |
| C—10-aldehyde (10% in propylene glycol | 10 |
| | 970 |

An addition of 30 parts of 3-ethyl-6-methyl-5-octen-2-one oxime brings substantially more volume to this base; it becomes softer, more flowery and at the same time much fresher.

After 24 hours, a very distinct green character can be established. The base is much more clinging compared with the original base.

EXAMPLE 11

Perfumery cologne:

| | Parts by weight |
|---|---|
| DPG | 265 |
| Bergamot oil | 200 |
| Linalyl acetate | 100 |
| Linalool | 80 |
| Lemon oil Italian | 80 |
| α-Amylcinnamaldehyde | 50 |
| Methyl dihydrojasmonate | 30 |
| α-Ionone | 30 |
| Geraniol | 30 |
| Citral | 20 |
| Eugenol | 20 |
| Tree moss absolute | 20 |
| Mandarin oil | 5 |
| Rosemary oil | 5 |
| Castoreum synthetic | 5 |
| Ylang oil | 5 |
| Indole (10% in DPG) | 5 |
| | 950 |

An addition of 50 parts of 3-ethyl-6-methyl-5-octen-2-one oxime produces a much greater intensity in this cologne. The base becomes much greener, more powerful, but also more flowery; it also clings much longer.

The novel substance exhibits here a very good effect which combines the different elements. The composition is much more harmonious by the addition of 3-ethyl-6-methyl-5-octen-2-one oxime.

I claim:

1. A compound of the formula

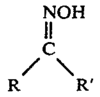
I wherein:

R is a $\Delta^{3,4}$ alkenyl group of six to twelve carbons, and

R' is an alkyl group of one to four carbons, provided that the total number of carbon atoms in the compound is between eleven and fourteen.

2. A compound according to claim 1 wherein the compound has a total of from eleven to thirteen carbon atoms.

3. A compound according to claim 1 wherein the compound has a total of eleven or twelve carbon atoms.

4. A compound according to claim 1 identified as 2,4,4,6-tetramethyl-6-hepten-3-one oxime.

5. A compound according to claim 1 identified as 3-ethyl-6-methyl-5-octen-2-one oxime.

6. A compound according to claim 1 identified as 3,3,6-trimethyl-5-octen-2-one oxime.

7. A compound according to claim 1 identified as 2,4,4,7-tetramethyl-6-octen-3-one oxime.

8. A compound according to claim 1 identified as 5-ethyl-7-nonen-4-one oxime.

9. A compound according to claim 1 identified as 4,7-dimethyl-6-nonen-3-one oxime.

10. A compound according to claim 1 identified as 2,2,7-trimethyl-6-nonen-3-one oxime.

11. An odorant composition comprising an olfactorily effective amount of a compound of the formula

I wherein:

R is a $\Delta^{3,4}$ alkenyl group of six to twelve carbons, and

R' is an alkyl group of one to four carbons, provided that the total number of carbon atoms in the compound is between eleven and fourteen and at least one other olfactory agent.

12. A composition according to claim 11 wherein the compound has a total of eleven or twelve carbon atoms.

13. A composition according to claim 11 wherein there is present at least one of the compounds selected from the group consisting of 2,4,4,6-tetramethyl-6-hepten-3-one oxime, 3-ethyl-6-methyl-5-octen-2-one oxime, 3,3,6-trimethyl-5-octen-2-one oxime, 2,4,4,7-tetramethyl-6-octen-3-one oxime, 5-ethyl-7-nonen-4-one oxime, 4,7-dimethyl-6-nonen-3-one oxime and 2,2,7-trimethyl-6-nonen-3-one oxime.

14. A method for improving the odor of fragrance compositions which comprises adding thereto an olfactorily effective amount of a compound of the formula

I wherein:

R is a $\Delta^{3,4}$ alkenyl group of six to twelve carbons, and

R' is an alkyl group of one to four carbons, provided that the total number of carbon atoms in the compound is between eleven and fourteen.

15. A method according to claim 14 wherein there is added a compound which has a total of eleven or twelve carbon atoms.

16. A method according to claim 14 wherein there is added at least one of the compounds selected from the group consisting of 2,4,4,6-tetramethyl-6-hepten-3-one oxime, 3-ethyl-6-methyl-5-octen-2-one oxime, 3,3,6-trimethyl-5-octen-2-one oxime, 2,4,4,7-tetramethyl-6-octen-3-one oxime, 5-ethyl-7-nonen-4-one oxime, 4,7-dimethyl-6-nonen-3-one oxime and 2,2,7-trimethyl-6-nonen-3-one oxime.

* * * * *

UNITED STATES PATENT AND TRADEMARK OFFICE

CERTIFICATE OF CORRECTION

PATENT NO. : 4,544,714

DATED : Oct. 1, 1985

INVENTOR(S) : Robert F. Tavares

It is certified that error appears in the above-identified patent and that said Letters Patent is hereby corrected as shown below:

The term of this patent subsequent to January 17, 2001, has been disclaimed.

Signed and Sealed this

Twenty-seventh Day of June, 1989

*Attest:*

DONALD J. QUIGG

*Attesting Officer*

*Commissioner of Patents and Trademarks*